United States Patent
Sani et al.

(10) Patent No.: US 10,695,309 B2
(45) Date of Patent: Jun. 30, 2020

(54) SUSTAINED-RELEASE LIOTHYRONINE FORMULATIONS, METHOD OF PREPARATION AND METHOD OF USE THEREOF

(71) Applicant: Western New England University, Springfield, MA (US)

(72) Inventors: Shabnam N. Sani, Grafton, MA (US); Hamid Bakhteyar, Raleigh, NC (US)

(73) Assignee: WESTERN NEW ENGLAND UNIVERSITY, Springfield, MA (US)

(*) Notice: Subject to any disclaimer, the term of this patent is extended or adjusted under 35 U.S.C. 154(b) by 0 days.

(21) Appl. No.: 15/941,644

(22) Filed: Mar. 30, 2018

(65) Prior Publication Data

US 2018/0280330 A1 Oct. 4, 2018

Related U.S. Application Data

(60) Provisional application No. 62/479,725, filed on Mar. 31, 2017.

(51) Int. Cl.
| | |
|---|---|
| *A61K 31/197* | (2006.01) |
| *A61K 9/48* | (2006.01) |
| *A61P 5/14* | (2006.01) |
| *A61K 9/00* | (2006.01) |

(52) U.S. Cl.
CPC .......... *A61K 31/197* (2013.01); *A61K 9/0053* (2013.01); *A61K 9/485* (2013.01); *A61K 9/4825* (2013.01); *A61K 9/4858* (2013.01); *A61K 9/4866* (2013.01); *A61P 5/14* (2018.01)

(58) Field of Classification Search
CPC .. A61K 31/197; A61K 9/4866; A61K 9/4858; A61K 9/485; A61K 9/4825; A61P 5/14
See application file for complete search history.

(56) References Cited

U.S. PATENT DOCUMENTS

| | | | |
|---|---|---|---|
| 4,369,172 | A | 1/1983 | Schor et al. |
| 4,952,402 | A | 8/1990 | Sparks et al. |
| 4,973,304 | A | 11/1990 | Graham et al. |
| 5,009,895 | A | 4/1991 | Lui |
| 5,324,522 | A | 6/1994 | Krenning et al. |
| 6,500,459 | B1 | 12/2002 | Chhabra et al. |
| 8,268,352 | B2 | 9/2012 | Vaya et al. |
| 8,404,281 | B2 | 3/2013 | Rubin et al. |

(Continued)

FOREIGN PATENT DOCUMENTS

| | | |
|---|---|---|
| WO | 9818610 A1 | 5/1998 |
| WO | 9943307 A1 | 9/1999 |

(Continued)

OTHER PUBLICATIONS

Capsule Connection, "Capsule Size", retrieved from https://capsuleconnection.com/capsule-sizing-info/ on May 3, 2019. (Year: 2019).*

(Continued)

*Primary Examiner* — Jianfeng Song
(74) *Attorney, Agent, or Firm* — Cantor Colburn LLP

(57) ABSTRACT

Disclosed herein are sustained release Liothyronine oral capsule formulations, methods of making the formulations and use to treat hypothyroidism, a thyroid deficient disease state, or thyroid dysfunction.

17 Claims, 5 Drawing Sheets

(56) References Cited

U.S. PATENT DOCUMENTS

Figure 1:
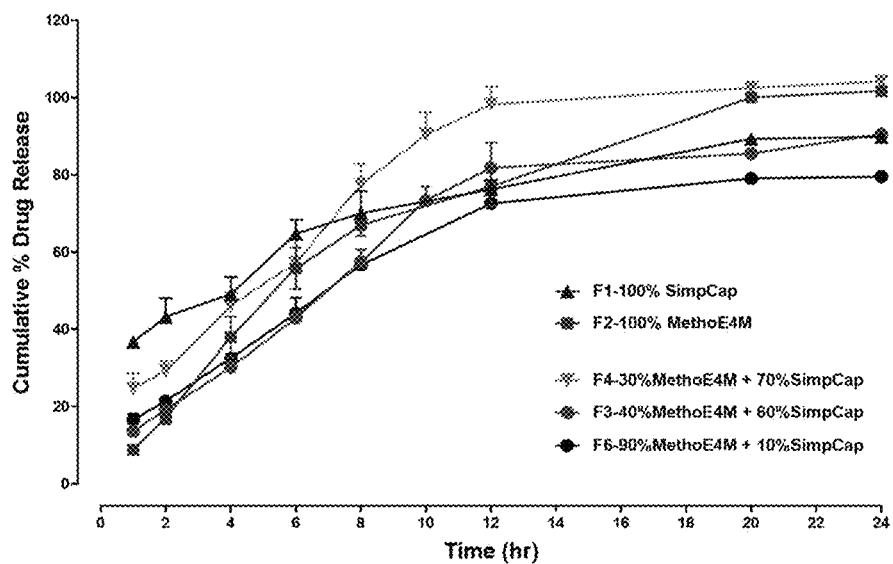

| | | | |
|---|---|---|---|
| 8,455,619 | B2 | 6/2013 | Latham |
| 8,460,702 | B2 | 6/2013 | Smith et al. |
| 9,381,255 | B2 | 7/2016 | Rubin et al. |
| 9,427,406 | B2 | 8/2016 | Gavryushin et al. |
| 9,526,701 | B2 | 12/2016 | Latham |
| 2003/0133982 | A1 | 7/2003 | Heimlich et al. |
| 2003/0198672 | A1 | 10/2003 | Franz et al. |
| 2004/0152783 | A1 | 8/2004 | Olon et al. |
| 2005/0148556 | A1* | 7/2005 | Tawakol .............. A61K 9/4866 514/165 |
| 2006/0018934 | A1 | 1/2006 | Vaya et al. |
| 2006/0246133 | A1* | 11/2006 | Beasley .............. A61K 9/2054 424/468 |
| 2007/0254920 | A1* | 11/2007 | deLong ................ C07C 69/608 514/319 |
| 2008/0008750 | A1* | 1/2008 | Tochio .................... A61J 3/072 424/454 |
| 2009/0130202 | A1 | 5/2009 | Smith et al. |
| 2010/0130723 | A1 | 5/2010 | Latham |
| 2010/0136109 | A1 | 6/2010 | Ross et al. |
| 2013/0157992 | A1 | 6/2013 | Latham |
| 2013/0243868 | A1 | 9/2013 | Rubin et al. |
| 2015/0079184 | A1 | 3/2015 | Gavryushin et al. |

FOREIGN PATENT DOCUMENTS

| | | | |
|---|---|---|---|
| WO | 0170218 | A1 | 9/2001 |
| WO | 03082188 | A2 | 10/2003 |
| WO | 2004071432 | A2 | 8/2004 |
| WO | 2005048979 | A2 | 6/2005 |
| WO | 2007068948 | A2 | 6/2007 |
| WO | 2007125295 | A2 | 11/2007 |
| WO | 2008051291 | A2 | 5/2008 |
| WO | 2008057464 | A2 | 5/2008 |
| WO | 2013006402 | A1 | 1/2013 |

OTHER PUBLICATIONS

Cassone, C. et al.; "Formulation, Evaluation, and Characterization of the In Vitro Release Kinetics of Compounded Slow Release Capsules of Liothyronine Sodium (T3)" AAPS Meeting Abstract Nov. 16, 2016 (1 page).

Dow Chemical Company; "Using Dow Excipients for Controlled Release of Drugs in Hydrophilic Matrix Systems"; Form No. 198-02075-0906 AMS; Published Sep. 2006; pp. 1-36.

Dow Chemical Company; "Using METHOCEL Cellulose Ethers for Controlled Release of Drugs in Hydrophilic Matrix Systems"; Form No. 198-02075-700 AMS; Jul. 2000; pp. 1-36.

Freedom SimpleCap Powder Sep. 19, 2013.

Freedom SimpleCap Powder Certificate of Analysis Oct. 18, 2017.

IPE, LLC; "A Study of Sustained-Release Liothyronine Sodium(T3) in Healthy Subjects"; pharmacokinetics of oral T3 Liothyronine Sodium (T3; triiodothyronine); https://clinicaltrials.gov/ct2/show/NCT01581463; last update posted Aug. 6, 2012.

Jonklaas, J. et al.; "Guidelines for the Treatment of Hypothyroidism"; Prepared by the American Thyroid Association Task Force on Thyroid Hormone Replacement; 2014; pp. 1-207.

Jonklaas, J. MD, PhD et al.; "Single Dose T3 Administration: Kinetics and Effects on Biochemical and Physiologic Parameters"; Ther Drug Monit, vol. 37, No. 1. Feb. 2015. pp. 110-118.

Milner, Martin; "Hypothyroidism: Optimizing Medication with Slow-Release Compounded Thyroid Replacement"; International Journal of Pharmaceutical Compounding, vol. 9, No. 4; Jul./Aug. 2005; pp. 268-273.

Reier, Dr. George E.; "Avicel PH Microcrystalline Cellulose, NF, Ph Eur., JP, BP"; FMC Corporation, Section 11; 2000; pp. 1-27.

Western New England University; "70th Annual Eastern Colleges Science Conference"; Apr. 2, 2016; pp. 1-116.

Bakhteyar et al., Int. J. Pharm. Compounding, vol. 21, No. 5, 418-425, Sep.-Oct. 2017.

Cole, Graham; "Evaluating Development and Production Costs: Tablets versus Capsules"; Pharmaceutical Technolog Europe, vol. 5, pp. 17-26, 1998.

Ullmann, Patricia; "Excipient selection for compounded pharmaceutical capsules: they're only fillers, right?"; Australian Journal of Pharmacy, vol. 98, No. 1164, Aug. 2017, p. 78-83.

* cited by examiner

SUSTAINED-RELEASE LIOTHYRONINE FORMULATIONS, METHOD OF PREPARATION AND METHOD OF USE THEREOF

CROSS-REFERENCE TO RELATED APPLICATION

This application claims the benefit of U.S. Provisional Application No. 62/479,725, filed Mar. 31, 2017, which is incorporated herein in its entirety.

BACKGROUND

Liothyronine (T3), along with its precursor levothyroxine (T4), have often been prescribed, alone or in combination, for the initial treatment of clinical underactive thyroid in hormone replacement therapy. Underactive thyroid, is the prevalent disease-state hypothyroidism, a common condition in which the thyroid gland neglects to produce sufficient amounts of thyroid hormones. This condition precipitates life-altering, and potentially life threatening symptomology in approximately 5.8 million people within the United States, as reported by the American Association of Clinical Endocrinologists (AACE) including ataxia, intractable chronic fatigue, bradycardia, cold intolerance, hyperlipidemia, mental impairment, weight gain, impaired concentration, and depression.

Currently, T3 is commercially available as 5, 25, and 50 microgram immediate-release (IR) tablets of liothyronine sodium (Cytomer), which are typically administered up to 2-4 times daily. T3 is a biologically active moiety that is rapidly absorbed into the bloodstream with a high reported bioavailability (69-99%). T3 is 3-4 times more potent as compared to T4; yet exhibits a relatively short half-life of less than 2 days, versus that of T4 (6-7 days). Thus, following the administration of any IR formulation, T3 plasma levels often fluctuates, which leads to inconsistent and often undesired serum levels. In addition, some patients can be under or over treated using the only available three dosages.

The benefits and drawbacks of commercially available formulations of T3 have been studied in the past. Recent studies have also reviewed the effectiveness of T4 and T3 as the single active ingredient versus a fixed amount of T3 and T4 as a combination therapeutic. Most recently, it has been shown that a slow-release T3 or a specific blend of T4 with slow-release T3 may grant more benefit to the patients and resolve many of the limitations on patients' quality of life. These results indeed have highlighted the individual needs of patients and have brought to the spotlight the fact that one size does not fit all. Compounded T4, T3, or a combination thereof at mathematical ratios other than 4.22:1 can help a certain patient population who otherwise will be therapeutic failures.

Despite available hormone replacement therapy stategies, still a significant percentage of patients with hypothyroidism and thyroid dysfunctionality remain symptomatic. There is continued need in the art for sustained release T3 formulations that maintain stable concentrations of T3, such that daily administration of T3 provides steady serum levels of T3.

SUMMARY

In an embodiment, a sustained release oral capsule formulation comprises a capsule fill comprising liothyronine or a pharmaceutically acceptable salt thereof, a hydroxypropyl methylcellulose, and a filler; the liothyronine or a pharmaceutically acceptable salt thereof is present in an amount equivalent to about 0.1 to about 25 micrograms of liothyronine; about 25 to about 95% wt of a hydroxypropyl methylcellulose based on the total weight of the hydroxypropyl methylcellulose and filler, wherein the hydroxypropyl methylcellulose has 19-30% methoxyl content, 7-12% hydroxypropoxyl content, and 3000-120000 cP apparent viscosity as a 2% solution in water at 20° C.; and about 5 to about 75% wt of a filler based on the total weight of the hydroxypropyl methylcellose and filler, wherein the filler is lactose or microcrystalline cellulose; wherein the capsule formulation exhibits a Zero order or Higuchi release kinetic pattern.

In another embodiment, a method of treating comprises administering a sustained release oral capsule formulation comprising liothyronine or a pharmaceutically acceptable salt thereof to a patient in need thereof for the treatment of a disease or condition, wherein the disease or condition is hypothyroidism, a thyroid deficient disease state, or thyroid dysfunction, and wherein the sustained release oral capsule formulation comprises a capsule fill comprising liothyronine or a pharmaceutically acceptable salt thereof, a hydroxypropyl methylcellulose, and a filler; the liothyronine or a pharmaceutically acceptable salt thereof is present in an amount equivalent to about 0.1 to about 25 micrograms of liothyronine; about 25 to about 95% wt of a hydroxypropyl methylcellulose based on the total weight of the hydroxypropyl methylcellulose and filler, wherein the hydroxypropyl methylcellulose has 19-30% methoxyl content, 7-12% hydroxypropoxyl content, and 3000-120000 cP apparent viscosity as a 2% solution in water at 20° C.; and about 5 to about 75% wt of a filler based on the total weight of the hydroxypropyl methylcellose and filler, wherein the filler is lactose or microcrystalline cellulose; wherein the capsule formulation exhibits a Zero order or Higuchi release kinetic pattern.

The above described and other features are exemplified by the following figures and detailed description.

In general, the disclosure may alternately comprise, consist of, or consist essentially of, any appropriate components herein disclosed. The disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

DRAWINGS

Referring now to the figures, which are exemplary embodiments and not to be considered limiting:

FIG. 1. Dissolution profiles of various METHOCEL E4M and SIMPLECAP capsule formulations (F1-F6).

Figure 2:
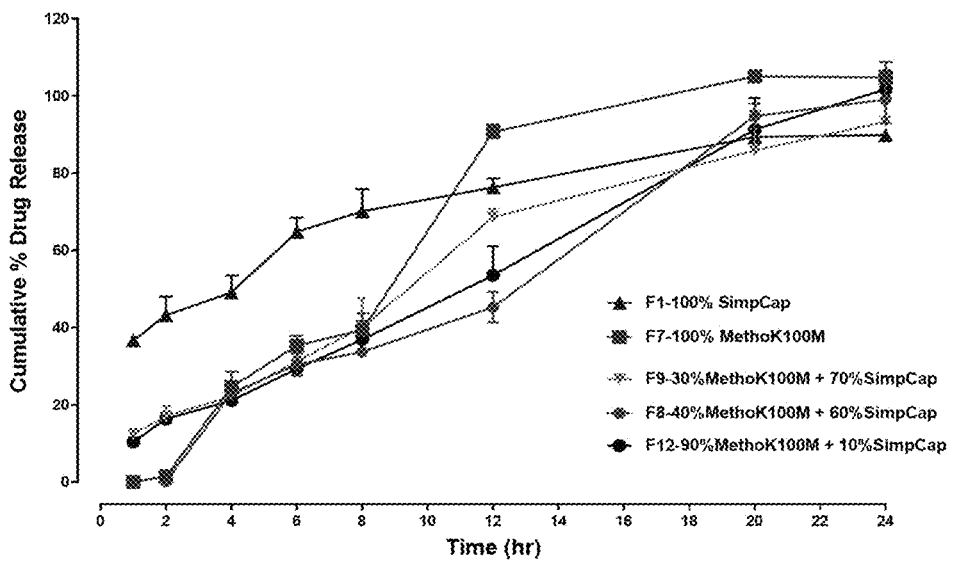

FIG. 2. Dissolution profiles of various METHOCEL K100M and SIMPLECAP capsule formulations (F7-F12).

Figure 3:
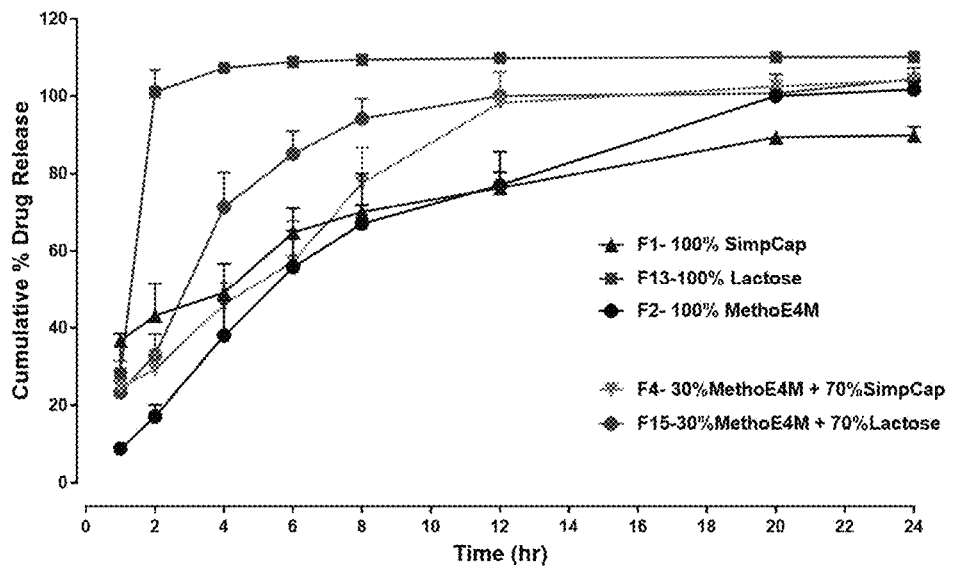

FIG. 3. A comparison of two different capsule formulations utilizing 30% METHOCEL E4M.

Figure 4:
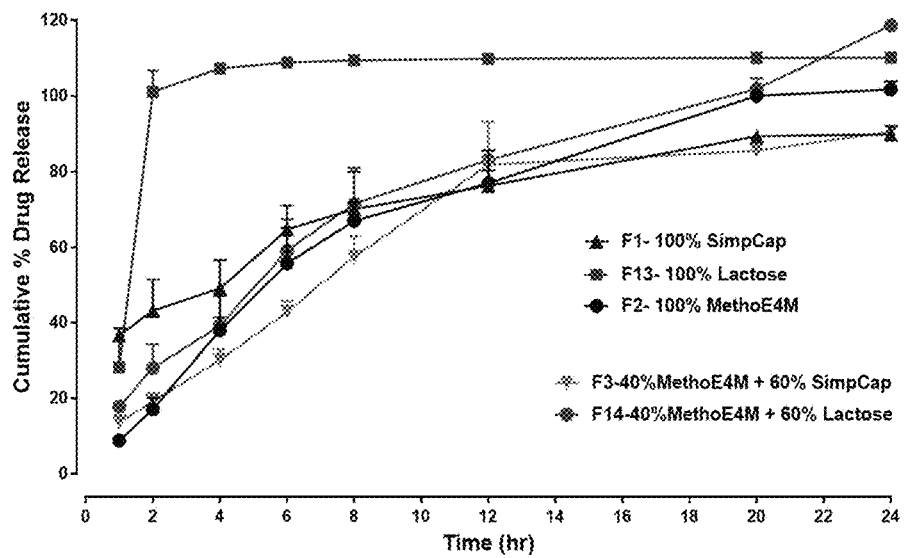

FIG. 4. A comparison of two different capsule formulations utilizing 40% METHOCEL E4M.

Figure 5:
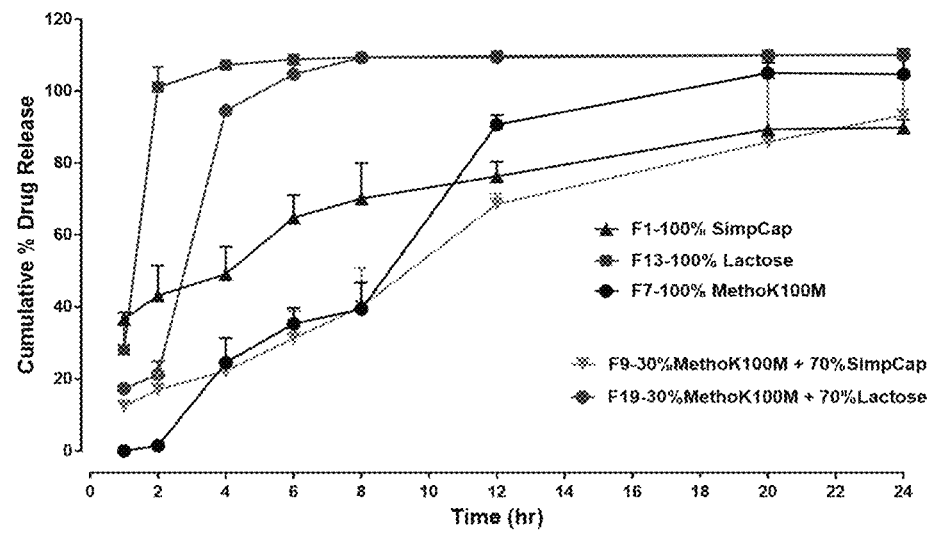

FIG. 5. A comparison of two different capsule formulations utilizing 30% METHOCEL K100M.

Figure 6:
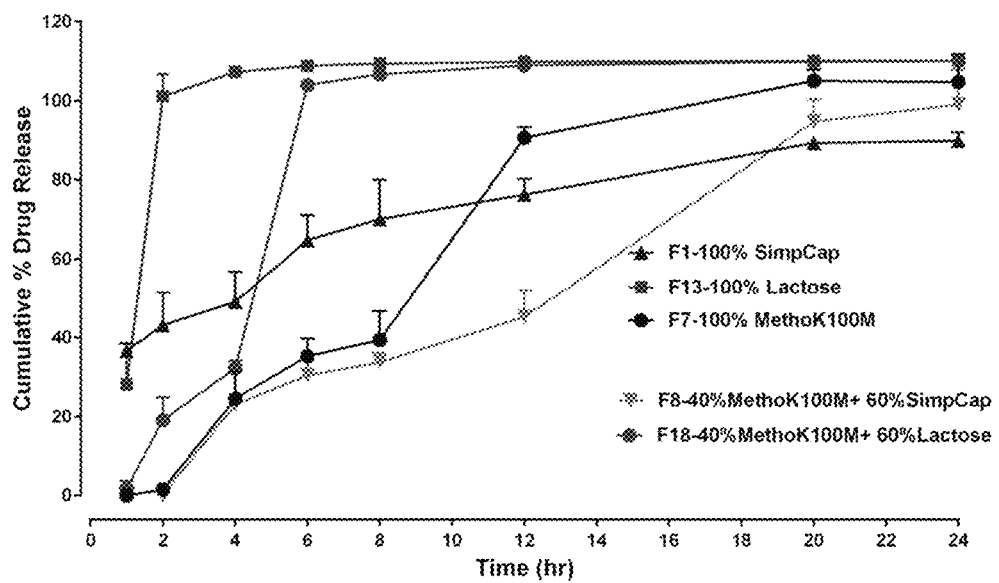

FIG. 6. A comparison of two different capsule formulations utilizing 40% METHOCEL K100M.

Figure 7:
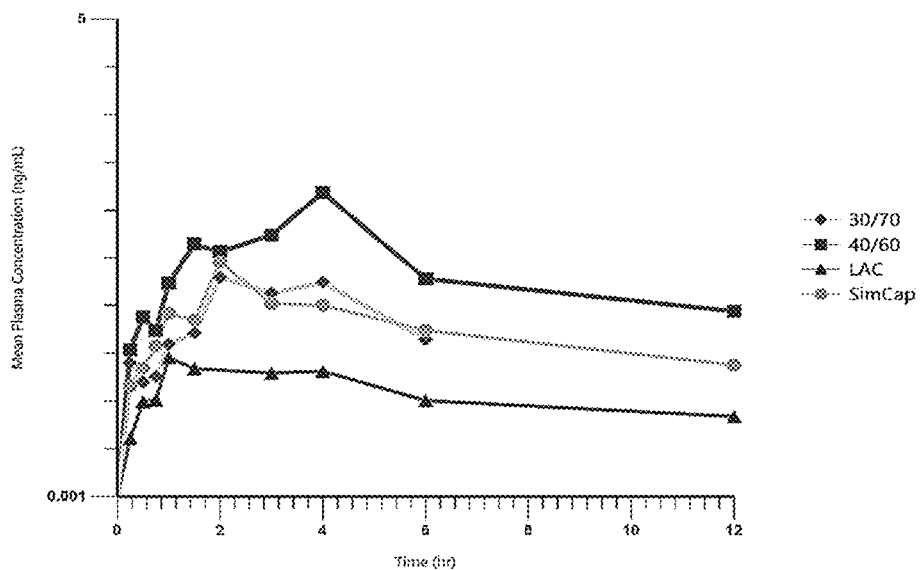

FIG. 7. Plasma concentration time profiles of four capsule formulations (F1, F3, F4, and F13).

Figure 8:
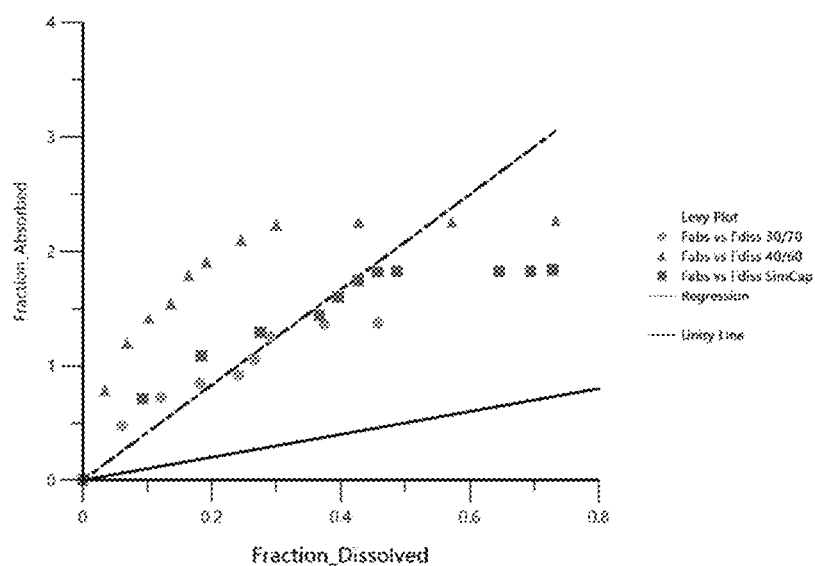
Figure 9:
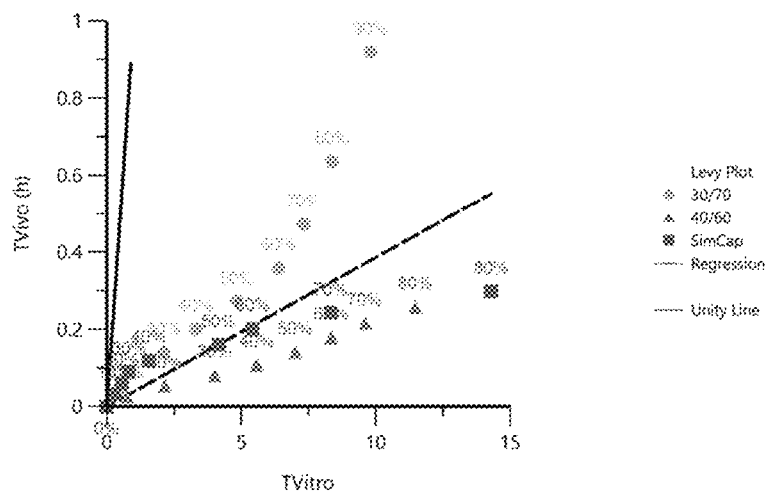
Figure 10:
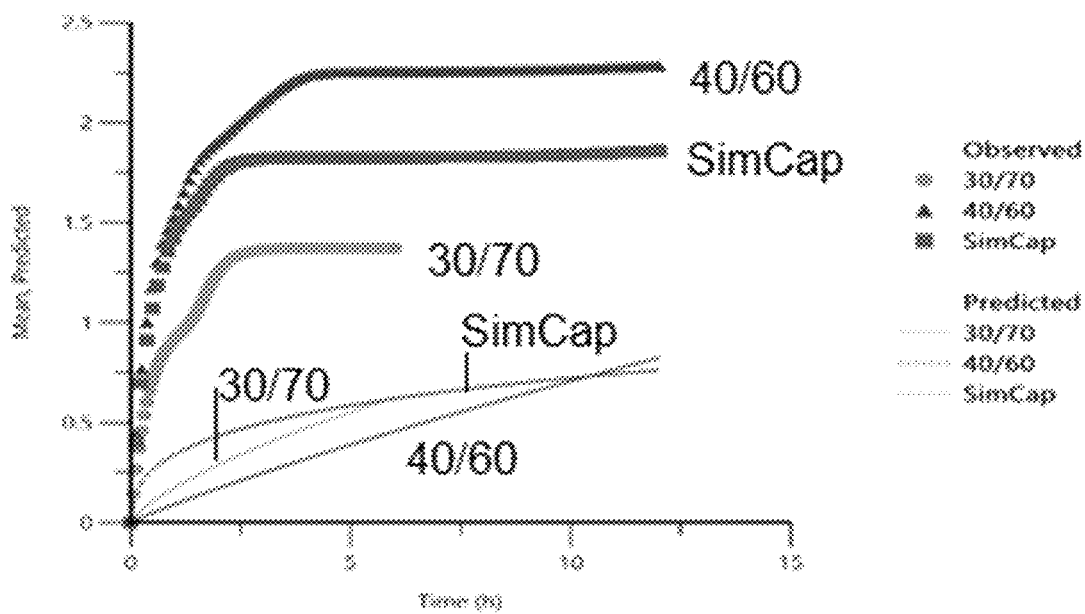

FIG. 8. Levy plots of Fdiss vs. Fabs.
FIG. 9. Levy plots of Tvitro vs. Tvivo.
FIG. 10. Model validation using internal formulations.

DETAILED DESCRIPTION

The slow-release (SR) T3 oral capsules (alternatively "sustained release") disclosed herein are an improvement over commercially available, immediate release dosage form of T3 as they can be prepared to achieve targeted serum levels of free T4 and T3 while minimizing adverse side effects. The slow-release oral capsules provide prolonged drug release over several hours, which can result in decreasing dosing frequency, obtaining more constant plasma concentration levels, and reducing adverse effects, which ultimately translates into improving the overall clinical efficacy. Customized dosage forms of T3 and T4 allow for dose adjustments in order to achieve a desirable balance of necessary T3 and T4 which in turn leads to achieve an optimal health and resolution of the symptoms. By compounding an optimal and precise amount of T3 and/or T4 SR formulation, the patients' overall health and well-being will be improved by giving the clinician the ability to achieve targeted serum levels and desirable therapeutic objective while minimizing the adverse drug effects. For many patients this is also associated with the improvement of the symptoms and "feeling better" (cold tolerance, foggy thinking, regulating menses in women, etc.).

Disclosed herein are sustained release oral capsule formulations comprising a capsule shell and a capsule fill, the capsule fill comprising liothyronine or a pharmaceutically acceptable salt thereof, a sustained release matrix excipient to control the release kinetics of the Liothyronine or a pharmaceutically acceptable salt thereof, a filler, and optionally an additional pharmaceutically acceptable excipient. The capsule fill composition is selected to result in the capsule formulation exhibiting a Zero order or Higuchi release kinetic pattern. These release patterns can be characterized, for example, by in vitro or in vivo drug release studies. In one embodiment, the release kinetic pattern is determined using an in vitro drug release study to measure the formulation's dissolution release profile as described herein.

Suitable dosage strengths of the sustained release capsule formulations can be about 0.1 to about 25 micrograms of liothyronine or a pharmaceutically acceptable salt thereof, specifically about 0.5 to about 20 micrograms, more specifically about 1 to about 15 micrograms, and yet more specifically about 3 to about 10 micrograms of liothyronine or a pharmaceutically acceptable salt thereof per dosage unit. Exemplary dosage strengths include about 1, about 2, about 3, about 5, about 7.5, about 10, about 12.5, about 15, about 17.5, about 20, or about 25 micrograms T3 (equivalent liothyronine acid) per dosage unit, specifically as a salt such as liothyronine sodium.

In an embodiment, the sustained release capsule formulations consist of liothyronine or a pharmaceutically acceptable salt thereof as the only active agent present in the capsule. In another embodiment, the sustained release capsule formulations comprise liothyronine or a pharmaceutically acceptable salt thereof and levothyroxine (T4).

"Dosage unit" means a single unit dosage form for administration. In an example, a capsule formulation is a single unit dosage form. By "oral dosage form" is meant to include a unit dosage form for oral administration. In an embodiment, the dosage unit is a capsule shell filled with a capsule fill in the form of a homogeneous powder blend of active agent, a sustained release matrix excipient, a filler, and optionally an additional pharmaceutically acceptable excipient. A dosage unit may optionally comprise a plurality of subunits such as, for example, granules, particles, pellets, microcapsules, microtablets, and the like. Multiple subunits may be combined or packaged for administration in a single dose.

The sustained release matrix excipient of the capsule fill can be, for example, a carbomer, cellulose acetate, an alkyl cellulose (e.g. ethylcellulose, methylcellulose), a hydroxyalkyl cellulose (e.g. a hydroxypropyl cellulose), a hydroxylalkyl alkylcellulose (e.g. a hydroxypropyl methylcellulose), a polyacrylate polymer (e.g. EUDRAGIT RL100 and EUDRAGIT RS100), a polyacrylic acid, a polyvinyl alcohol, a polyvinylpyrrolidone, and the like, or a combination thereof.

In an embodiment, the sustained release matrix excipient is a hydroxylalkyl alkylcellulose, for example, a hydroxypropyl methylcellulose, including the commercially available METHOCEL materials described herein. Use of hydroxypropyl methylcellulose for sustained release tablets is known, although there is little discussion for its use in non-tablet and non-compressed sustained release formulations such as capsule formulations where the capsule fill material is not compressed or compacted. In an embodiment, the capsule fill of the sustained release capsule formulations disclosed herein is a loose fill and not compressed prior to encapsulation and not compressed by the encapsulation process.

METHOCEL is a commercially available group of water-soluble, cellulose ether polymers, specifically hydroxypropyl methylcellulose polymers. This group of polymers functions as a controlled-release excipient by decreasing the rate of drug release via the continuous hydration and formation of a gel barrier. The polymer level should be sufficient enough to form a uniform gel barrier to a desirable degree. This barrier protects the drug to be released immediately into the dissolution media. The mechanisms by which drug release is controlled is determined by diffusion (if soluble) through the gel and/or by the rate of erosion. Higher aqueous solubility of the drug (T3 is highly soluble in alkaline environment) generally leads to a higher diffusion driving force and faster release profile as is observed in a capsule formulation of T3 and lactose (100%).

METHOCEL E4M is a grade of hydroxypropyl methylcellulose commercially available from The Dow Chemical Company having a 28-30% methoxyl content, 7-12% hydroxypropoxyl content (USP substitution type 2910), 3000-5600 cP apparent viscosity 2% solution in water at 20° C.; and 2308-3755 mPa·s apparent viscosity 2% solution in water at 20° C.

METHOCEL K100M is a grade of hydroxypropyl methylcellulose commercially available from The Dow Chemical Company having a 19-24% methoxyl content, 7-12% hydroxypropoxyl content (USP substitution type 2208), 80000-120000 cP apparent viscosity 2% solution in water at 20° C.; and 16922-19267 mPa·s apparent viscosity 2% solution in water at 20° C.

METHOCEL E10M is a grade of hydroxypropyl methylcellulose commercially available from The Dow Chemical Company having a 28-30% methoxyl content, 7-12% hydroxypropoxyl content (USP substitution type 2910), 7500-14000 cP apparent viscosity 2% solution in water at 20° C.; and 4646-7070 mPa·s apparent viscosity 2% solution in water at 20° C.

METHOCEL K15M is a grade of hydroxypropyl methylcellulose commercially available from The Dow Chemical Company having a 19-24% methoxyl content, 7-12% hydroxypropoxyl content (USP substitution type 2208), 11250-21000 cP apparent viscosity 2% solution in water at 20° C.; and 6138-9030 mPa·s apparent viscosity 2% solution in water at 20° C.

METHOCEL K4M is a grade of hydroxypropyl methylcellulose commercially available from The Dow Chemical Company having a 19-24% methoxyl content, 7-12% hydroxypropoxyl content (USP substitution type 2208), 3000-5600 cP apparent viscosity 2% solution in water at 20° C.; and 2308-3755 mPa·s apparent viscosity 2% solution in water at 20° C.

The sustained release matrix excipient is present in the capsule fill in an amount of about 1 to about 100 percent weight (% wt), specifically at least 5, 10, 15, 20, 25, 30, 35, 40, 45, 50, 55, 60, 65, 70, 75, 80, 85, 90, 95, or 100% wt or any amount or range therein based on the total weight of the capsule fill or based on the total weight of the capsule fill excluding the active agent weight. Suitable ranges of sustained release matrix excipient amounts include, for example, about 5 to about 95% wt, about 10 to about 90% wt, about 15 to about 85% wt, about 20 to about 80% wt, about 25 to about 75% wt, about 30 to about 70% wt, about 35 to about 65% wt, about 40 to about 60% wt, about 45 to about 55% wt, or about 5 to about 95% wt based on the total weight of the capsule fill or based on the total weight of the capsule fill excluding the active agent weight.

Exemplary suitable fillers include inert pharmaceutical diluents such as calcium carbonate, calcium phosphate, dextrose/glucose, fructose, lactitol, lactose, magnesium carbonate, maltodextrin, maltose, mannitol, microcrystalline cellulose, polydextrose, sorbitol, sucrose, trehalose, xylitol, and the like, or a combination thereof.

In an embodiment the filler is lactose. In another embodiment, the filler is microcrystalline cellulose.

The filler can be present in the capsule fill in an amount of about 0 to about 99% wt, specifically at least 1, 5, 10, 15, 20, 25, 30, 35, 40, 45, 50, 55, 60, 65, 70, or 75% wt or any amount or range therein based on the total weight of the capsule fill or based on the total weight of the capsule fill excluding the active agent weight. Suitable ranges of filler amounts include, for example, about 1 to about 75% wt, about 2 to about 70% wt, about 3 to about 65% wt, about 4 to about 60% wt, about 5 to about 55% wt, about 7.5 to about 50% wt, about 10 to about 45% wt, about 12 to about 40% wt, about 15 to about 35% wt, about 20 to about 30% wt, about 25 to about 30% wt or about 5 to about 75% wt based on the total weight of the capsule fill or based on the total weight of the capsule fill excluding the active agent weight.

The capsule fill of the sustained release capsule formulation can optionally further comprise an additional pharmaceutically acceptable excipient. Exemplary suitable additional pharmaceutically acceptable excipients include a glidant, a disintegrant, a lubricant, a combination thereof, and the like. In an embodiment, an excipient mixture can comprise a premix of a filler, a glidant, a disintegrant, a lubricant, or a combination thereof.

Exemplary suitable glidants include colloidal silicon dioxide, precipitated silica, silica gel, and the like, or a combination thereof, specifically colloidal silicon dioxide. Glidants can be present in the capsule fill in an amount of about 0 to about 2% wt, specifically about 0.1 to about 1% wt, and more specifically about 0.25 to about 0.5% wt based on the total weight of the capsule fill or based on the total weight of the capsule fill excluding the active agent weight.

Exemplary suitable disintegrants include alginic acid, carboxymethylcellulose calcium, carboxymethylcellulose sodium, powdered cellulose, chitosan, croscarmellose sodium, crospovidone, guar gum, methyl cellulose, sodium alginate, sodium starch glycolate, a starch (e.g. maize, potato, pregelatinized, tapioca, etc.), and the like, or a combination thereof; specifically sodium starch glycolate. Disintegrants can be present in the capsule fill in an amount of about 0 to about 15% wt, specifically about 1 to about 10% wt, and more specifically about 2 to about 5% wt based on the total weight of the capsule fill or based on the total weight of the capsule fill excluding the active agent weight.

Exemplary suitable lubricants include calcium stearate, glycerol behenate, magnesium stearate, mineral oil, polyethylene glycol, sodium stearyl fumarate, stearic acid, talc, vegetable oil, zinc stearate, and the like, or a combination thereof; specifically sodium stearyl fumarate or magnesium stearate; and more specifically sodium stearyl fumarate. Lubricants can be present in the capsule fill in an amount of about 0 to about 5% wt, specifically about 0.5 to about 3% wt, and more specifically about 1 to about 2% wt based on the total weight of the capsule fill or based on the total weight of the capsule fill excluding the active agent weight.

The additional pharmaceutically acceptable excipient(s) can be present in the capsule fill in an amount of about 0 to about 20% wt, specifically no more than 19, 17, 15, 13, 11, 10, 9, 8, 7, 6, 5, 4, 3, 2, or 1% wt or any amount or range therein based on the total weight of the capsule fill or based on the total weight of the capsule fill excluding the active agent weight.

In another embodiment, the filler is premixed with an additional pharmaceutically acceptable excipient, such as a glidant, a disintegrant, a lubricant, and the like or a combination thereof. In an exemplary embodiment, the filler is microcrystalline cellulose premixed with an additional pharmaceutically acceptable excipient. SIMPLECAP is a capsule and tablet excipient composite comprised of filler, glidant, disintegrant and lubricant commercially available from Fagron, Inc. (formerly Freedom Pharmaceuticals, Inc.) SIMPLECAP contains microcrystalline cellulose, silicon dioxide colloidal, sodium starch glycolate, and sodium stearyl fumarate. Another suitable premix is PROSOLV EASYtab SP commercially available by JRS Pharma containing microcrystalline cellulose, silicon dioxide colloidal, sodium starch glycolate, and sodium stearyl fumarate.

The capsule fill can be encapsulated in a capsule prepared from suitable materials including pharmaceutically acceptable gelling agents, for example gelatin or a plant polysaccharide such as carrageenan, modified starch, or modified cellulose. The capsule shell can further contain a plasticizer, a coloring agent, a preservative, a disintegrant, a lubricant, and the like, or a combination thereof. In an exemplary embodiment, the capsule is a hard gelatin capsule.

In one embodiment, the release kinetic pattern of the sustained release oral capsule formulation is determined using an in vitro drug release study to measure the formulation's dissolution release profile. A dissolution profile is a plot of the cumulative amount of active agent released as a function of time. A dissolution profile can be measured utilizing the Drug Release Test <724>, which incorporates standard test USP 26 (Test <711>). A profile is characterized by the test conditions selected such as, for example, apparatus type, shaft speed, temperature, volume, and pH of the dissolution medium. More than one dissolution profile may be measured. For example, a first dissolution profile can be measured at a pH level approximating that of the stomach, and a second dissolution profile can be measured at a pH level approximating that of one point in the intestine or several pH levels approximating multiple points in the intestine.

A highly acidic pH may be employed to simulate the stomach and a less acidic to basic pH may be employed to simulate the intestine. By the term "highly acidic pH" is meant a pH of about 1 to about 4. A pH of about 1.2, for example, can be used to simulate the pH of the stomach. By the term "less acidic to basic pH" is meant a pH of greater than about 4 to about 7.5, specifically about 6 to about 7.5. A pH of about 6 to about 7.5, specifically about 6.8, can be used to simulate the pH of the intestine.

In an embodiment, the in vitro dissolution release profile of the sustained release capsules were evaluated utilizing a USP paddle (type II) apparatus (DISTEK model 2100C, North Brunswick, N.J.) at a temperature of 37° C.±0.2° C. and RPM of 50±0.1 per minute. The dissolution media consisted of 1000 mL of Phosphate Buffered Saline (PBS) (pH=7.3±0.1). Release can be measured for any duration of time, including from time point 0 to up to 24 hours, specifically every hour, and more specifically at time points of 0, 1, 2, 4, 6, 8, 12, 20, and 24 hours. In an embodiment, the SR formulation is tested in triplicate. The cumulative percentage of drug release for the formulation can be fitted to known release kinetic equations to determine the best fitting model of drug release as well as the mechanism of release.

In an embodiment, the sustained release capsule formulation exhibits an in vitro dissolution profile that is substantially a Zero order or Higuchi release kinetic pattern when tested using a USP paddle (Type II) apparatus at a temperature of 37° C.±0.2° C. and RPM of 50±0.1 per minute using 1000 mL phosphate buffered saline (pH=7.3±0.1) as the dissolution medium.

The sustained release capsule may be characterized by its dissolution properties. Dissolution may also be tested at different pHs. In an embodiment, the dissolution profile of the sustained release capsule when tested using a USP paddle (Type II) apparatus at a temperature of 37° C.±0.2° C., RPM of 50±0.1 per minute and 1000 mL phosphate buffered saline (pH=7.3±0.1) as the dissolution medium is: about 20 to about 30% release at 1 hour, about 50 to about 60% release at 6 hours, and about 90 to about 100% release at 12 hours. Optionally further within this embodiment, the sustained release capsule formulation exhibits a dissolution profile of about 25 to about 35% release at 2 hours, about 40 to about 50% release at 4 hours, about 75 to about 85% release at 8 hours, about 80 to about 95% release at 10 hours, and about 95 to about 100% release at 20 hours.

In an embodiment, a sustained release oral capsule formulation comprises a capsule shell and a capsule fill, the capsule fill comprising liothyronine or a pharmaceutically acceptable salt thereof, a hydroxypropyl methylcellulose, and a filler; the liothyronine or a pharmaceutically acceptable salt thereof is present in an amount equivalent to about 0.1 to about 25 micrograms of liothyronine; about 25 to about 95% wt of a hydroxypropyl methylcellulose based on the total weight of the hydroxypropyl methylcellulose and filler, wherein the hydroxypropyl methylcellulose has 19-30% methoxyl content, 7-12% hydroxypropoxyl content, and 3000-120000 cP apparent viscosity as a 2% solution in water at 20° C.; and about 5 to about 75% wt of a filler based on the total weight of the hydroxypropyl methylcellulose and filler, wherein the filler is lactose or microcrystalline cellulose; and wherein the capsule formulation exhibits a Zero order or Higuchi release kinetic pattern.

A sustained release capsule formulation comprising liothyronine sodium with METHOCEL E4M (100%) exhibited slow release kinetic patterns of Zero Order when evaluated in an in vitro dissolution analysis tested using a USP paddle (Type II) apparatus at a temperature of 37° C.±0.2° C. and RPM of 50±0.1 per minute using 1000 mL phosphate buffered saline (pH=7.3±0.1) as the dissolution medium. Under the same in vitro dissolution analysis conditions a sustained release capsule formulation comprising liothyronine sodium with 30% METHOCEL E4M and 70% SIMPLECAP released 100% of the drug within the initial 12 hours and exhibited a Zero Order slow release kinetic pattern. Further under the same in vitro dissolution analysis conditions, the following sustained release capsule formulations comprising liothyronine sodium followed a slow release kinetic pattern of Zero Order or Higuchi: 40% METHOCEL K100M+ 60% SIMPLECAP; 50% METHOCEL K100M+ 50% SIMPLECAP; 30% METHOCEL E4M+ 70% Lactose; 90% METHOCEL E4M+ 10% Lactose; 40% METHOCEL K100M+ 60% Lactose; and 50% METHOCEL K100M+ 50% Lactose.

Optimal T3 formulations depend upon the patients' symptomology and target plasma levels. Generally, formulations that exhibit a slower release rate may hold greater benefit to patients' who have achieved their optimal T3 plasma concentration, whereas if a patients' plasma level is low, a slow release formulation that exhibits greater initial elevation may best suit the patients' need. For the patients, the optimal formulation will depend upon each individual's specific target plasma levels and symptoms.

The sustained release capsule formulations herein may benefit the patients who have already achieved their optimal plasma T3 concentration and need a long-term maintenance of T3 plasma levels.

The sustained release capsule formulations herein described can be administered to a patient in need thereof for the treatment of a disease or condition, wherein the disease or condition is hypothyroidism, a thyroid deficient disease state, or thyroid dysfunction.

This invention is further illustrated by the following examples that should not be construed as limiting.

EXAMPLES

Example 1

Kinetic Analysis of Drug Release from Compounded Slow-Release Capsules of Liothyronine (T3) Sodium Materials: Liothyronine (T3) sodium (Lot 06302015: 2122) was purchased from Sigma Aldrich, USA. Blue locking gelatin capsules #3, USP (Lot 1401210060) purchased from Letco Medical Inc. (Decatur, Ala.). METHOCEL E4M (hypromellose 2910 USP (Lot F10623-3, 17)), METHOCEL K100M (hypromellose 2208 USP (Lot F11146) premium CR), Lactose Monohydrate (Lot F11226-05, 06), and Freedom SIMPLECAP powder (Lot F10865-4 and Lot 15D01-F001) were donated by Freedom® Pharmaceuticals Inc. (Broken Arrow, Okla.). Triiodothyronine enzyme-linked immunosorbent assay (ELISA) kits were purchased from Sigma-Aldrich (model SE120132: St. Louis, Mont.) and Abcam Inc. (model AB108685, Cambridge, Mass.). Purified water was from a Direct-Q® 3 UV laboratory water purification system (model No.

F1CA39722). Phosphate Buffered Saline (PBS) Tablet USP (Lot 74199080A) was purchased from Gibco™ (Waltham, Mass.).

Experimental Design: T3 capsules (7.5 μg Liothyronine sodium active ingredient) were compounded at Carolina Compounding Pharmacy & Health Center, Cary, N.C. All preparations were compounded under the supervision of Dr. Hamid Bakhteyar (the registered pharmacist member of the research team). The compositions of the various formulations examined in this study are summarized in Table 1. In Groups 1 and 3, different compositions of METHOCEL E4M with SIMPLECAP/or Lactose were tested, whereas in Groups 2 and 4, METHOCEL K100M was utilized as the primary excipient in combination with SIMPLECAP/or Lactose.

TABLE 1

| Group No. | Formulation ID | Composition |
| --- | --- | --- |
| 1 | F1 (control) | T3 + SIMPLECAP (100%) |
| 1 | F2 (control) | T3 + Methocel E4M (100%) |
| 1 | F3 | T3 + Methocel E4M (40%) + SIMPLECAP (60%) |
| 1 | F4 | T3 + Methocel E4M (30%) + SIMPLECAP (70%) |
| 1 | F5 | T3 + Methocel E4M (50%) + SIMPLECAP (50%) |
| 1 | F6 | T3 + Methocel E4M (90%) + SIMPLECAP (10%) |
| 2 | 7 (control) | T3 + Methocel K100M (100%) |
| 2 | F8 | T3 + Methocel K100M (40%) + SIMPLECAP (60%) |
| 2 | F9 | T3 + Methocel K100M (30%) + SIMPLECAP (70%) |
| 2 | F10 | T3 + Methocel K100M (50%) + SIMPLECAP (50%) |
| 2 | F12 | T3 + Methocel K100M (90%) + SIMPLECAP (10%) |
| 3 | F13 (control) | T3 + Lactose (100%) |
| 3 | F14 | T3 + Methocel E4M (40%) + Lactose (60%) |
| 3 | F15 | T3 + Methocel E4M (30%) + Lactose (70%) |
| 3 | F16 | T3 + Methocel E4M (50%) + Lactose (50%) |
| 3 | F17 | T3 + Methocel E4M (90%) + Lactose (10%) |
| 4 | F18 | T3 + Methocel K100M (40%) + Lactose (60%) |
| 4 | F19 | T3 + Methocel K100M (30%) + Lactose (70%) |
| 4 | F20 | T3 + Methocel K100M (50%) + Lactose (50%) |
| 4 | F21 | T3 + Methocel K100M (90%) + Lactose (10%) |

Preparation of Liothyronine Sodium (7.5 μg) slow-release capsules: Liothyronine sodium and all other excipients were weighed using an analytical balance. Aliquot method of weighing was utilized to make T3 capsules. The powder mixture was blended using a V-mixer machine for 10 minutes to ensure content uniformity. Capsules were filled at batches of 50 using a capsule machine USP size #3. Three lots of each formulation were randomly selected for the dissolution studies.

Performing quality assessment of slow-release capsules: Quality control assessments including weight variation and content uniformity tests, dissolution of capsules, active drug assay, physical appearance, and physical stability were performed on all formulations. Weight variation and content uniformity was conducted according to USP chapter <795> (The United States pharmacopeia. 2015; 38(4)). According to USP, the compounded preparations are to be prepared to ensure that each contains no less than 90.0% and no more than 110.0% of the theoretically calculated and labeled quantity of active ingredient per unit of the preparation. Additionally, a representative number of dosage units (10 capsules) should weigh no less than 90% and no more than 110% of the average weight of all capsules in the batch and the relative standard deviation should be below 6%. The content uniformity assay was also conducted on 10 individual capsules from each formulation bath. The capsules were then shipped to Western New England University, College of Pharmacy, for further characterization.

Sample Assay method: Samples were analyzed for T3 concentrations by commercially available ELISA kits. The assays were conducted in direct accordance with the manufacturer's instructions verified for in vitro use. Assay sensitivity was achieved in the ng/mL range (0-7.5 ng/mL) which correlated well with physiological plasma range of T3. The absorbance was measured spectrophotometrically at 450 nm wavelength, using a (BioTek® Model ELX808 Winooski, Vt.) spectrophotometer. Validation of each kit was based upon comparison between serial dilutions of standardized test samples with the reproducible standard calibration curve (0-7.5 ng/mL) provided by the manufactures of the kit. A blank control of PBS buffer was included in triplicate in the assay plates to examine any significant absorbance interference by the dissolution media components.

Drug release experiments: The in vitro dissolution of the various extemporaneously compounded SR capsules were evaluated utilizing a United States Pharmacopeia (USP) paddle (type II) apparatus (DISTEK model 2100C, North Brunswick, N.J.) at a temperature of 37° C.±0.2° C. and RPM of 50±0.1 per minute. The dissolution media consisted of 1000 mL of PBS (pH=7.3±0.1). Each formulation was tested in triplicate. Samples were withdrawn at given time points of 0, 1, 2, 4, 6, 8, 12, 20, and 24 hours.

Data Analysis: The amount of T3 in each time point within the 24-hour interval was utilized to calculate percentage release of T3 versus time. The calculated cumulative percent release was plotted with respect to time and the standard deviations were calculated using GraphPad Prism®, version 7 (CA, USA). Cumulative percentage of drug release for each formulation was fitted to the eleven most common release kinetic equations (Table 2) to find out the best model of drug release profile as well as the mechanism of drug release. The mathematical equations for the models used to describe the dissolution profiles are summarized in Table 2 where Q is the percent of drug released at time t and $k_0$, $k_1$, $k_h$ and $k_p$ are the coefficients of the equations. An empirical equation of Korsmeyer-Peppas model $[Q=k_p(t)^n]$ was utilized to describe general solute behavior from controlled-release polymeric matrices where n is the release exponent indicative of the mechanism of release. When n approximates between 0.43-0.50 (Higuchi release kinetics), a Fickian/diffusion-controlled release is implied, whereas a $0.5<n<1.0$ value indicates a non-Fickian transport. If the value of n approaches 1.0, phenomenologically one may conclude that the release is approaching Zero Order kinetic, an ultimate goal for a slow-release delivery system. The best-fit model for each formulation was identified by evaluating the coefficient of determination (RSQ) and mean percent error (MPE) using the following equation:

$$MPE = \frac{100 \times \sum \frac{|Fcak - Fobs|}{Fobs}}{N}$$

Where Fobs and Fcal are the measured and calculated fraction of the drug released in each sampling time, and N is the number of sampling times. For a given release profile, the highest RSQ value and smallest MPE values indicated the best fit model.

TABLE 2

| Kinetics | Equation* |
|---|---|
| Zero order | $Q = k_0 t$ |
| Higuchi model (1963) | $Q = k_h (t)^{0.5}$ |
| Korsmeyer-Peppas model (1983) | $Q = k_p (t)^n$ |
| First Order | $Ln (1 - Q) = -k_1 t$ |
| Hixon-Crowell | $1 - \sqrt[3]{1 - Q} = k_{1/3} t$ |
| Weibull | $Ln[-Ln(1 - Q)] = \beta Ln\, t_d + \beta Ln t$ |
| Wagner Linear | $Z = Z_0 + qt$ |
| Wagner Log Probability | $Z' = Z_0' + q'Ln\, t$ |
| Square root of mass | $1 - \sqrt{1 - Q} = k_{1/2}\, t$ |
| Three seconds root of mass | $1 - \sqrt[3]{(1 - Q)^2} = k_{2/3} t$ |
| Non-conventional order 1 | $1 - (1 - Q)^{1-n} = (1 - n) k_{1-n}\, t$ |

*Q denotes the percent of drug released at time t. $k_0$, $k_1$, $k_p$, p, k, $k_{1/3}$, $k_{1/2}$, $k_{2/3}$, $t_d$, β, $Z_0$, $Z_0'$, q, and q' are parameters of the models. Z and Z' are probits of fraction of drug released at any time. $Z_0$ and $Z_0'$ are the values of Z and Z' when t = 0 and t = 1, respectively.

Results: The cumulative percent release of T3 for various formulations was plotted with respect to time and the standard deviations were calculated for each time point within 24 hrs (FIGS. 1-6). Moreover, for each formulation, the cumulative percentage of the release was fitted to eleven major release kinetic equations listed in Table 2. The results of the kinetic analysis and the best model fit for formulations 1-21 are summarized in Table 3.

TABLE 3

| Group No. | Formu- lation | Best fit model | Max RSQ | MPE | k | n |
|---|---|---|---|---|---|---|
| 1 | F1 | Peppas | 0.998 | 0.457 | 0.368 | 0.205 |
| 1 | F2 | Peppas~Zero Order | 0.999 | 2.210 | 0.087 | 1.036 |
| 1 | F3 | Wagner Linear | 0.999 | 1.831 | 0.184 | — |
| 1 | F4 | Zero Order | 0.990 | 3.992 | 0.072 | — |
| 1 | F5 | Square Root of Mass | 0.998 | 1.110 | — | — |
| 1 | F6 | Three seconds root of mass | 0.997 | 2.285 | — | — |
| 2 | F7 | Hixon-Crowell | 0.956 | 41.936 | — | — |
| 2 | F8 | Peppas~Higuchi | 0.992 | 1.825 | 0.103 | 0.584 |
| 2 | F9 | Wagner Linear | 0.987 | 9.053 | 0.1223 | — |
| 2 | F10 | Peppas~Higuchi | 0.992 | 1.825 | 0.103 | 0.584 |
| 2 | F12 | Peppas | 0.983 | 5.807 | 0.101 | 0.620 |
| 3 | F13 | — | — | — | — | — |
| 3 | F14 | Hixon-Crowell | 0.986 | 4.02 | — | — |
| 3 | F15 | Peppas~Higuchi | 1 | 0 | 0.2300 | 0.502 |
| 3 | F16 | Peppas | 0.978 | 8.89 | 0.0945 | 0.818 |
| 3 | F17 | Zero Order | 0.994 | 5.35 | 0.0446 | — |
| 4 | F18 | Higuchi | 0.994 | 12.03 | 0.318 | — |
| 4 | F19 | Peppas | 1 | 0 | 0.1740 | 0.278 |
| 4 | F20 | Peppas~Zero Order | 0.959 | 10.94 | 0.0834 | 0.973 |
| 4 | F21 | Peppas | 0.972 | 2.05 | 0.3777 | 0.221 |

FIG. 1 displays the release profiles of the formulations composed of METHOCEL E4M and SIMPLECAP with varing percentage (ranging from 10%-100%) of the excipients (F1-F6, note: for simplicity selective, more informative plots have been shown). In both F1 (100% SIMPLECAP) and F2 (100% METHOCEL E4M) approximately 75% of the T3 was released within initial 12 hrs. F1 and F2 both exhibited slow-release kinetic profiles of Peppas Power Law and Zero Order, respectively. While F1 (100% SIMPLECAP) exhibited a higher percentage of drug release within the initial six hrs compared to F2 (100% METHOCEL E4M), yet, ultimately 80% of the total T3 content was releasd after 24 hrs; wheras F2 showed 100% drug release within 24 hrs. Additionally, by increasing the percentage of METHOCEL E4M, the release rate slope shifted to the right indicating a slower release rate in general. When SIMPLECAP (60%) was combined with 40% METHOCEL E4M (as in F3), 80% of the drug release over 24 hours period, remained the same as seen with SIMPLECAP alone while exhibiting a Linear Probability release kinetics. The reduction of the percentage of METHOCEL E4M from 40% to 30% (as in F4) has increased the total release from 80% to 100% within a 12 hour duration with a Zero Order kinetic release profile. Overall, the formulation with lower percentage of METHOCEL E4M (i.e. F4 with 30% METHOCEL E4M+ 70% SIMPLECAP) exhibited a higher percentage of drug release within 8-12 hrs as compared to F1, F2, F3 and F6. A formulation with the highest percentage (90%) of METHOCEL E4M (F6), released only 70% of the drug content within 12 hrs while displaying a Three Seconds Root of Mass slow-release release kinteics. F6 and F3 showed a similar profile within the initial 7 hrs where 50% of the drug content was released from both formulations.

The release profiles of formulations containing various percentage of METHOCEL K100M and SIMPLECAP are shown in FIG. 2 (note: for simplicity selective, more informative plots have been shown). When T3 was formulated with 100% METHOCEL K100M, the percentage of drug release within the initial 2 hrs was negligible and only 40% release was occured within 8 hours; yet, the majority of the release took place between 8-12 hrs with a release plateau of 100% after 12 hrs. In general, the release patterns with METHOCEL K100M seemed to be much slower within the initial 8 hrs; by increasing percentage of the METHOCEL K100M, the release rate slope was shifted to the right indicating of a slower release. When SIMPLECAP was combined with 30% METHOCEL K100M as exhibited in F9, Linear Probability slow-release kinetics was observed where 70% of the drug was released within 12 hours; a slower release pattern than that of formulation F4 (30% METHOCEL E4M+70% SIMPLECAP), and reached 90% release within 24 hours. Fomulations F8 (40% METHOCEL K100M+60% SIMPLECAP) and F12 (90% METHOCEL K100M+10% SIMPLECAP) exhibited similar release profiles with respcet to time; both formulations released 50% of the drug in 12 hours and 100% after 24 hours.

The kinetic profiles of formulations containing a substitution of Lactose for SIMPLECAP were also explored for all formulations shown in Table 1 with only selective results displayed in FIGS. 3-6. As expected, the formulation containing solely 100% Lactose (F13) was an immediate release formulation where 100% of the release occured over the initial 2 hours (FIG. 3). F15 (30% METHOCEL E4M+ 70% Lactose) exhibited a Higuchi slow-release kinetic pattern where similar to F4 (30% METHOCEL E4M+ 70% SIMPLECAP), 100% of the drug was released within 12 hrs; yet, F15 exhibited a much higher percentage of drug release within the initial 2-8 hrs as compared to the respective times of F4; although both formulations exhibited slow-release kintetic patterns of Higuchi and Zero order, respectively (FIG. 3).

FIG. 4 shows the release profiles of formulations containing either SIMPLECAP or Lactose with 40% METHOCEL E4M. Similar to FIG. 3, F14 (40% METHOCEL E4M+ 60% Lactose) had a higher percentage of drug release observed within 1-8 hrs as compared to the F3 (40% METHOCEL E4M+ 60% SIMPLECAP), although both formulations exhibited slow-release kintetic patterns of Hixon-Crowell and Wagner Linear respectively.

In FIGS. 5 and 6, the kinetic profiles of either SIMPLECAP or Lactose with 30% and 40% METHOCEL K100M are depicted. Both F9 (30% METHOCEL K100M+ 70% SIMPLECAP) and F19 (30% METHOCEL K100M+ 70% Lactose) released only 20% of the drug within the initial 2 hrs, but the release rate was much faster afterwards with the Lactose containing formulations where 100% of the drug was released within 4 hrs. A 10% increase in the amount of METHOCEL K100 M as in F8 and F18 (FIG. 6) exhibited a similar release pattern with a more slower initial release of the drug.

Both formulations F8 (40% METHOCEL K100M+ 60% SIMPLECAP) and F18 (40% METHOCEL K100M+ 60% Lactose) exhibited Higuchi slow-release kinetics.

This study showed that both SIMPLECAP (100%) and METHOCEL E4M (100%) exhibit slow-release kinetic profiles of Peppas Power Law and Zero Order, respectively. Additionally, with an increasing percentage of METHOCEL E4M, the release rate slope shifted to the right indicating a slower release rate in general. When SIMPLECAP (70%) was combined with (30%) METHOCEL E4M, the total content of the drug (100%) was released within 12 hour with a Zero Order kinetic release profile as compared to 75% release within the same time period with 100% METHOCEL E4M.

When T3 was formulated with 100% METHOCEL K100M, the percentage of drug release within the initial 2 hrs was neglegible and only 40% release was occured within 8 hours. In general, the release patterns of formulation containing METHOCEL K100M were much slower within the initial few hours; by increasing percentage of the METHOCEL K100M, the release rate slope was shifted to the right indicating of a slower release. Not wishing to be bound by theory, but this result may be due to higher molecular weight of the polymer which results in higher apparent viscosity of the hydrated gel barrier.

F15, a formulation with 30% METHOCEL E4M+ 70% Lactose, exhibited a Higuchi slow-release kinetic pattern which was similar to F4 (30% METHOCEL E4M+ 70% SIMPLECAP) formulation where in both, 100% of the drug was released within a 12 hour duration; however the former exhibited a much higher percentage of drug release within the initial 2-8 hours, although both formulations exhibited slow-release kintetic patterns of Higuchi and Zero order, respectively. Both formulations of F8 (40% METHOCEL K100M+ 60% SIMPLECAP) and F18 (40% METHOCEL K100M+ 60% Lactose) exhibited Higuchi slow-release kinetics. It is worthwhile to note that for all other formulations, the release pattern was fitted to one of the eleven equations of slow-release pattern (see Table 3 for more details).

The results of this study demonstrated several sustained release capsule formulations of T3 having Zero order, Higuchi, and Peppas release kinetic patterns.

Example 2

In Vivo Pharmacokinetic Study of Formulations F1, F3, F4, and F13 in Rats

All animal experiments were approved by IACUC & IBC at Baystate Health, Springfield, Mass. Sprague Dawley rats were used to investigate the pharmacokinetic (PK) profiles of the selected formulations (F1=T3+SIMPLECAP (100%) ("SimCap"); F3=T3+Methocel E4M (40%)+SIMPLECAP (60%) ("40/60"); F4=T3+Methocel E4M (30%)+SIMPLECAP (70%) ("30/70"); and F13=T3+Lactose (100%) ("LAC"). Animals were cannulated at the jugular vein under anesthesia and drug was administered orally by gavage. Blood samples were collected at 0, 0.25, 0.5, 0.75, 1, 1.5, 2, 3, 4, 6, 12, and 24 hours. Plasma concentration data were analyzed using various PK models to trace any significant difference in PK parameters of the SR formulations as compared to each other and the immediate release preparation (e.g. F13 of Example 1). Phoenix NLME® (Version 7, Pharsight, CA, USA) software was used to perform in vivo PK analysis. All other statistical analyses were performed using GraphPadPrism® software.

Development of IVIVC model: IVIVC-Level A was performed in various stages including the development of correlation model and validation of the model. Two-stage numerical deconvolution method was utilized which involves deconvolution in the first stage to explore the time course of in vivo absorption. In the second stage, correlation was built between the in vitro drug release and in vivo drug absorption. Unit impulse response (UIR) was generated by using immediate release form of drug (F13). Three preliminary formulations F1, F3, and F4 were considered for the building of IVIVC model. Fraction of drug absorbed was estimated using the deconvolution through convolution method (Phoenix NLME® IVIVC Toolkit, Version 7, CA, USA) from the observed pharmacokinetic profiles for each formulation. The IVIVC model was developed by using a fraction of the drug absorbed and that of a fraction of drug dissolved. On the basis of developed IVIVC model, predicted fraction of drug absorbed was estimated from the observed fraction of drug dissolved. Two levy plots were considered during a model development, i.e., fraction of drug absorbed (Fabs) versus fraction of drug dissolved (Fdiss) and in vivo absorption time (Tvivo) versus in vitro dissolution time (Tvitro). In order to attempt level A correlation, the following linear correlation models were applied. Model 1: Fabs=Diss(Tvivo), Model 2: Fabs=AbsScale×Diss (Tscale×Tvivo), Model3: Fabs=AbsScale×Diss (Tscale×Tvivo−Tshift), Model 4:Fabs=AbsScale×[Diss(Tscale×Tvivo−Tshift)−AbsBase]].

In vivo Pharmacokinetics Results: The concentration-time profiles are presented in FIG. 7. Initial estimate of PK parameters was derived from non-compartmental analysis and visual inspection of concentration time profiles. One-compartment oral model with naïve-pooled and naïve-average methods were explored with various residual methods to determine the model which best fit to the data. One compartment oral model using naïve-pooled/multiplicative residual error provided a reasonable estimate of PK parameters based on the goodness of fit criteria. The final estimate of PK parameters are shown in Table 4 below.

TABLE 4

Final estimates of pharmacokinetics parameters based on one-compartmental oral model

| Parameter | Estimate | Units | CV % | Stderr |
|---|---|---|---|---|
| tvKa | 2.63 | 1/h | 14.33 | 0.38 |
| tvV | 2.67 | L | 6.01 | 0.16 |
| tvCl | 0.09 | (L/h) | 30.81 | 0.03 |

In vitro-In vivo correlation: Linear correlation models mentioned earlier in the method section were screened for all formulations. Levy plot of Fdiss vs. Fabs provided preliminary information about which correlation model should be considered for IVIVC. Levy plots shown in FIG. 8 indicate the deviation of the data points from the regression and unity lines. For formulations F3, F4, there were linear correlation until 40-50 percent of Fdiss and the data points deviated thereafter. Three other models were examined with the consideration of AbsScale, Tshift, and Tscale. Levy plot of Tvitro vs. Tvivo (FIG. 9) shows time taken for a percentage of dissolution and the same percentage of absorption. AIC and SBC criteria helped to choose the best model. Inclusion of scaling and shifting parameters did not improve the model significantly and therefore, the base model was considered as the preliminary final model to build in vitro-in vivo correlation. The validation of the model using internal formulations did not show a match between observed rate of absorption and the predicted one based on the developed model (FIG. 10); thus, the need for further examination of non-linear models is warranted.

Unless defined otherwise, technical and scientific terms used herein have the same meaning as is commonly understood by one of skill in the art to which this disclosure belongs.

The singular forms "a," "an," and "the" include plural referents unless the context clearly dictates otherwise. The endpoints of all ranges directed to the same characteristic or component are independently combinable and inclusive of the recited endpoint. The suffix "(s)" as used herein is intended to include both the singular and the plural of the term that it modifies, thereby including one or more of that term (e.g., the carrier(s) includes one or more carriers). The term "or" means "and/or" unless clearly indicated otherwise by context. The term "combination" is inclusive of blends, mixtures, and the like.

Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

"Optional" or "optionally" means that the subsequently described event or circumstance may or may not occur, and that the description includes instances where the event occurs and instances where it does not.

"About" or "approximately" as used herein is inclusive of the stated value and means within an acceptable range of deviation for the particular value as determined by one of ordinary skill in the art, considering the measurement in question and the error associated with measurement of the particular quantity (e.g., the limitations of the measurement system). For example, "about" can mean within one or more standard deviations.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention can include only some of the described embodiments. Accordingly, the invention is not to be seen as limited by the foregoing description, but is only limited by the scope of the appended claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

What is claimed is:

1. A sustained release oral capsule formulation, comprising:
    a capsule fill comprising liothyronine or a pharmaceutically acceptable salt thereof, a hydroxypropyl methylcellulose, and a filler;
    the liothyronine or a pharmaceutically acceptable salt thereof is present in an amount equivalent to about 0.1 to about 25 micrograms of liothyronine;
    about 25 to about 95% wt of a hydroxypropyl methylcellulose based on the total weight of the hydroxypropyl methylcellulose and filler, wherein the hydroxypropyl methylcellulose has 19-30% methoxyl content, 7-12% hydroxypropoxyl content, and 3000-120000 cP apparent viscosity as a 2% solution in water at 20° C.; and
    about 5 to about 75% wt of a filler based on the total weight of the hydroxypropyl methylcellose and filler, wherein the filler is lactose or microcrystalline cellulose;
    wherein the capsule formulation exhibits a Higuchi release kinetic pattern.

2. The capsule formulation of claim 1, comprising liothyronine sodium equivalent to about 1, about 2, about 3, about 5, about 7.5, about 10, about 12.5, about 15, about 17.5, about 20 or about 25 micrograms of liothyronine.

3. The capsule formulation of claim 1, wherein the hydroxypropyl methylcellulose has
    a 28-30% methoxyl content, 7-12% hydroxypropoxyl content, and a 3000-5600 cP apparent viscosity as a 2% solution in water at 20° C.; or
    a 19-24% methoxyl content, 7-12% hydroxypropoxyl content, 80000-120000 cP apparent viscosity as a 2% solution in water at 20° C.

4. The capsule formulation of claim 1, comprising
    about 30 to about 90% wt of the hydroxypropyl methylcellulose, and
    about 10 to about 70% wt of the filler.

5. The capsule formulation of claim 1, comprising
    about 30 to about 50% wt of the hydroxypropyl methylcellulose, and
    about 50 to about 70% wt of the filler.

6. The capsule formulation of claim 1, comprising
    about 85 to about 95% wt of the hydroxypropyl methylcellulose, specifically where the hydroxypropyl methylcellulose has a 28-30% methoxyl content, 7-12% hydroxypropoxyl content, and a 3000-5600 cP apparent viscosity as a 2% solution in water at 20° C.; and
    about 5 to about 15% wt of the filler, specifically where the filler is lactose.

7. The capsule formulation of claim 1, comprising
    about 25 to about 35% wt of the hydroxypropyl methylcellulose, specifically where the hydroxypropyl methylcellulose has a 28-30% methoxyl content, 7-12% hydroxypropoxyl content, and a 3000-5600 cP apparent viscosity as a 2% solution in water at 20° C.; and
about 65 to about 75% wt of the filler.

8. The capsule formulation of claim 1, comprising
about 35 to about 55% wt of the hydroxypropyl methylcellulose, specifically where the hydroxypropyl methylcellulose has a 19-24% methoxyl content, 7-12% hydroxypropoxyl content, 80000-120000 cP apparent viscosity as a 2% solution in water at 20° C.; and
about 65 to about 45% wt of the filler.

9. The capsule formulation of claim 1, comprising
about 40 to about 50% wt of the hydroxypropyl methylcellulose, specifically where the hydroxypropyl methylcellulose has a 19-24% methoxyl content, 7-12% hydroxypropoxyl content, 80000-120000 cP apparent viscosity as a 2% solution in water at 20° C.; and
about 60 to about 50% wt of the filler.

10. The capsule formulation of claim 1, wherein the capsule formulation exhibits an in vitro dissolution profile that is substantially a Higuchi release kinetic pattern when tested using a USP paddle (Type II) apparatus at a temperature of 37° C.±0.2° C. and RPM of 50±0.1 per minute using 1000 mL phosphate buffered saline (pH=7.3±0.1) as the dissolution medium.

11. The capsule formulation of claim 1, wherein the capsule formulation exhibits an in vitro dissolution profile when tested using a USP paddle (Type II) apparatus at a temperature of 37° C.±0.2° C. and RPM of 50±0.1 per minute using 1000 mL phosphate buffered saline (pH=7.3±0.1) as the dissolution medium of
about 20 to about 30% release at 1 hour,
about 50 to about 60% release at 6 hours, and
about 90 to about 100% release at 12 hours; and
optionally further wherein the capsule formulation exhibits an in vitro dissolution profile of
about 25 to about 35% release at 2 hours,
about 40 to about 50% release at 4 hours,
about 75 to about 85% release at 8 hours,
about 80 to about 95% release at 10 hours, and
about 95 to about 100% release at 20 hours.

12. The capsule formulation of claim 1, wherein the capsule is a number 3 capsule or a number 3 hard gelatin capsule.

13. The capsule formulation of claim 1, wherein the capsule comprises a fill weight that is no more than 325 mg.

14. The capsule formulation of claim 1, wherein the liothyronine salt is liothyronine sodium.

15. The capsule formulation of claim 1, which releases the liothyronine or pharmaceutically acceptable salt thereof over a period of about 12 to about 24 hours.

16. The capsule formulation of claim 1, wherein the capsule fill further comprises a glidant, a disintegrant, a lubricant, or a combination thereof.

17. The capsule formulation of claim 16, wherein the glidant is colloidal silicon dioxide, the disintegrant is sodium starch glycolate, and the lubricant is sodium stearyl fumarate.

* * * * *